United States Patent [19]

Goto

[11] Patent Number: 5,649,898

[45] Date of Patent: Jul. 22, 1997

[54] INSTRUMENT FOR MAKING LOAD REMOVING CAST

[75] Inventor: Takeshi Goto, Kurume, Japan

[73] Assignee: Castec Corporation, Kurume, Japan

[21] Appl. No.: 567,171

[22] Filed: Dec. 5, 1995

[30] Foreign Application Priority Data

Sep. 26, 1995 [JP] Japan .................. 7-270684

[51] Int. Cl.$^6$ .................. A61F 5/00
[52] U.S. Cl. .................. 602/6; 602/9
[58] Field of Search .................. 602/3, 8, 9, 13, 602/4, 5, 6, 10, 11

[56] References Cited

U.S. PATENT DOCUMENTS

| | | | |
|---|---|---|---|
| 2,875,752 | 3/1959 | Lovich | 602/10 |
| 4,565,250 | 1/1986 | Vasko | 168/12 |
| 4,888,225 | 12/1989 | Sandvig et al. | 601/11 X |
| 5,002,047 | 3/1991 | Sandvig et al. | 602/8 |
| 5,520,621 | 5/1996 | Edenbaum et al. | 602/8 |

FOREIGN PATENT DOCUMENTS

| | | |
|---|---|---|
| 5-5116 | 1/1993 | Japan . |
| 7-289582 | 11/1995 | Japan . |

OTHER PUBLICATIONS

The Journal of Bone and Joint Surgery, American Volume, Jul. 1967.

Primary Examiner—Richard J. Apley
Assistant Examiner—Kim M. Lee
Attorney, Agent, or Firm—Jacobson, Price, Holman & Stern, PLLC

[57] ABSTRACT

PTB cast is prepared by means of an instrument which makes a predetermined space between a sole of a foot held in the cast and a bottom of the cast, whereby the foot can be moved vertically so that a pushing-up action by the bottom of the cast toward the sole of the foot can be prevented, thereby providing a load removing effect. If the thickness of the space is changed, the load removing effect may be controlled.

2 Claims, 8 Drawing Sheets

1

INSTRUMENT FOR MAKING LOAD REMOVING CAST

TECHNICAL FIELD OF THE INVENTION

The present invention relates to an instrument for preparing PTB casts used for treatment of tibial fractures, that is, casts applied to an affected leg.

PRIOR ART

PTB cast (Patellar Tendon Bearing cast, so-called load bearing leg casts, hereinafter briefly called as "cast") as seen in FIG. 8 has broadly been employed to treat tibial fractures (fracture of a leg bone). This cast is used for bearing a patient's human body weight at pressured parts around the knee joints (portions of the patellar tendon and tibial condyle) shown with arrows in FIG. 9 in order to enable a knee joint to move or walk with a working cast after having affected the leg bone or at an early period after a surgical operation, thereby protecting the tibial fractured portion and not to effect an excessive load thereon.

However, there are still many unknown matters in regard to the effects of removal of load which is a significant purpose of the cast, and accordingly not a few of medical specialists feel dubious about the load removing effect. These specialists allow patients to rely on crutches for assisting the load removal over a long period of days even after having worn the cast for assisting the load removal.

In view of the above mentioned circumstances, the inventor and associates used a dynamic foot pressure analysis system which was first introduced in Japan in 1992 and measured the load removing effect of the cast, and made studies on the actual load removing effects. Then, the load removing effect brought about by the prior cast was about only 30% of the patient's human body weight. This data tells that 70% of his weight is, when walking, burdened as a load to him on his fractured leg, and it was found that the load removing effect by the broadly used cast was unsatisfied.

In an early healing period while the tibial fracture is not yet recovered, if the body weight is given upon a fractured limb, and the load removing effect is insufficient, the load force by the body weight is added as a disadvantageous pressure to the fractured part with a result in causing curing difficulties such as a shortening deformity of the fractured part or delaying a healing fracture. However, a theoretical idea to allow the knee joint to move or allow to control the walking as loaded at the early recovering time at which the cast aims, is very important for healing the tibial fracture. Therefore, if the cast decreases or enables to control as theoretically the load by the body weight to the fractured part of the leg, it may be expected that the usefulness thereby will become greater. In this sense, the necessity to improve the load removing effect of the cast has been highlighted as a focus of attention.

SUMMARY OF THE INVENTION

From the above stated viewpoint of an antecedent art, the present invention has been designed to provide a novel instrument which may make casts that excel in the load removing effect.

The reason why a satisfied load removing effect could not be obtained by means of the existing cast is that since the bearing of the body weight by the cast is insufficient, the load moves, at burdening, in the burdening direction of the leg within the cast, the foot is pushed up on its sole by a bottom of the cast. The inventor and associates made by test various embodiments of casts for a purpose of improving the load removing effect of the cast for the tibial fracture, and made appreciations and studies on the load removing effect by the dynamic foot pressure analysis system. When a test was prepared for a cast by means of an instrument enabling to make a predetermined space between the sole of the foot and the bottom of the cast, the foot was, during walking, moved or played along the length of a shin bone (in the loading direction of the body weight) in the cast, whereby the push-up by the bottom of the cast toward the sole of the foot could be prevented, and it was found that the load removing effect was largely improved. For easily and exactly comprehending the principle of improving the load removing effect of the PTB cast, the under mentioned state should be presumed.

Imagine a morning-glory or trumpet shaped instrument. If one of hands is got into the instrument at a flared mouth thereof, its arm is held by a conical interior of the instrument and can no farther go ahead. Herein, the trumpet shaped instrument corresponds to the cast, and the arm corresponds to the affected leg. A force making the hand go farther corresponds to a load by the body weight. Namely, with respect to the conventional cast for fractured leg, the prior art intended that the leg was supported in the interior cavity of the cast which was presumed as the hollow conical column. However, since the cast and the leg are very imperfect figures as the conical bodies, a dynamic bearing power is limited in itself, and the leg somewhat slides within the cast due to the body weight toward the sole of the foot. This sliding of the leg causes the push-up to the sole of the foot by the cast, and the push-up hampers the load removing effect. Therefore, by forming the space between the sole of the foot and the bottom of the cast, a factor of hampering the load removing effect can be taken away even if the leg slides within the cast. Thus the satisfied load removing effect can be made available. Further, when we tested the cast by changing the thickness of the space, it was proved that the load removing effect may be also controlled.

Thus, the present invention has been devised on the basis of our new finding, and this is an instrument which is to be fixed together with the foot with a casting plaster (i.e., a condition before applying a material to the patient around his leg) such that a predetermined space is formed between the sole of the foot and the bottom of the cast when wrapping the casting plaster to the patient around his foot. The cast prepared by the instrument has the excellent load removing effect.

As the embodiments of the instrument, there will be enumerated an embodiment fixed as it is attached to the sole of the foot (FIGS. 2, 5 and 6), and another embodiment held as it is attached to a heel, a portion of this embodiment being extended downward than the heel (FIG. 7).

Further, when attaching to the sole of the foot, if the instrument is an elastic member, the thickness of the space after having been secured is varied when walking between the sole of the foot and the bottom of the cast, so that load removing effect may be controlled thereby.

Known material may be applicable as the elastic member if it expands and contracts when walking in response to even a slight load, such as a sponge, a soft rubber or a bellows composed of a soft synthetic resin. The wider is the space, the better is the load absorbing efficiency, and so the bellows bag or the sponge are preferable.

The cast prepared by means of such an instrument is formed with the predetermined space therebetween. If the patient walks as attaching the thus made leg cast, the foot can be moved or played in the space along the length of the shin bone (in the loading direction) within the voluntarily predetermined range. This play absorbs an impact force or the load force caused by the load giving bad influences to the fractured bone of the leg, and the satisfied load removing effect is made available.

Figure 1A:
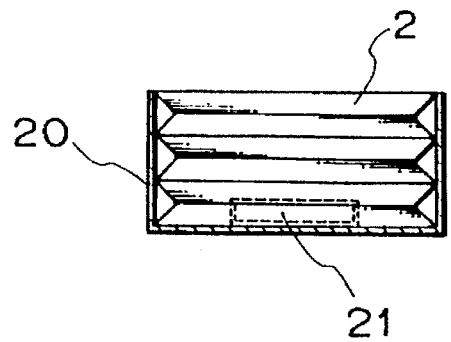
FIG. 1 shows a first embodied instrument, in which (a) is a front view of this embodiment, (b) is a plane view of the same, and (c) is a side view thereof.

In the drawings of FIGS. 1 through 9, the reference numeral 1 is the cast body, 2 is a bellows bag as an elastic member made of a soft resin, 3 is a foot, 4 is a space defined between the sole of the foot and the bottom of the cast by means of the present inventive instrument, 5 is a sponge, 6 is a spring, 7 is a protecting plate, 10 is a bottom of the cast, and 20 is a protecting case made of a hard resin.

PREFERRED EMBODIMENT OF THE INVENTION

Figure 1B:
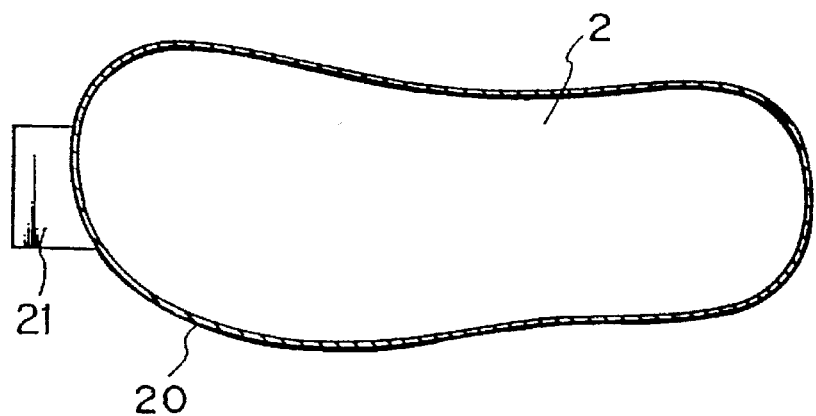
Figure 1C:
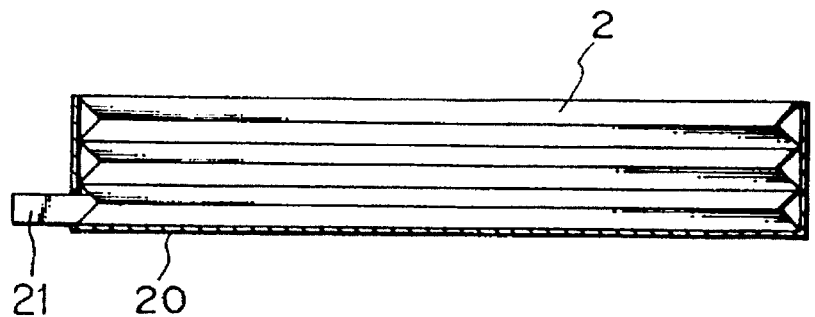
Figure 3A:
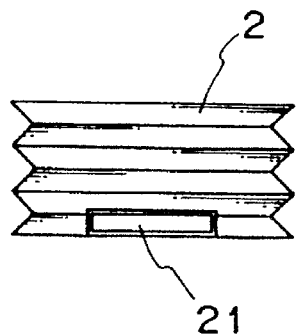
FIG. 3 explains the bellows bag, in which (a) is a front view of this embodiment, (b) is a plane view of the same, and (c) is a side view thereof.
Figure 3B:
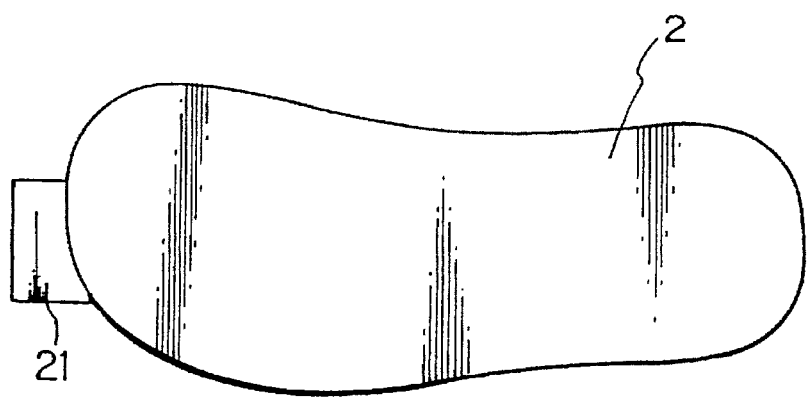
Figure 3C:
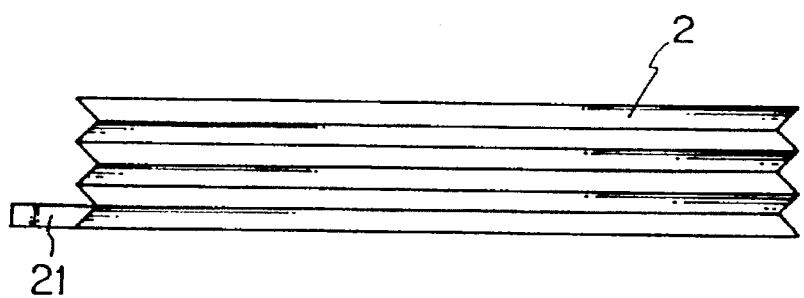
Figure 4A:
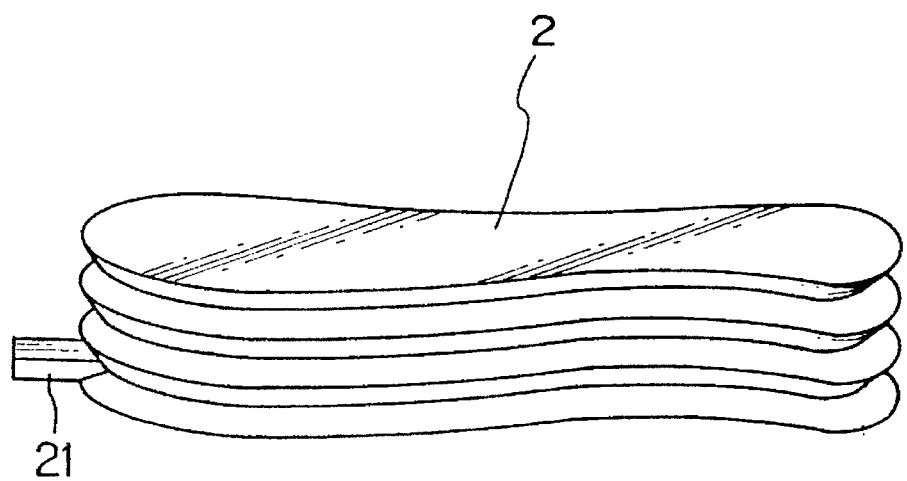
FIG. 4 shows expansion and contraction of the bellows bag, in which (a) is a case of the former, and (b) is a case of the latter.
Figure 4A:
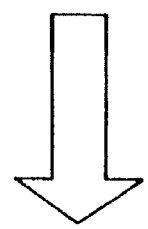
Figure 4B:
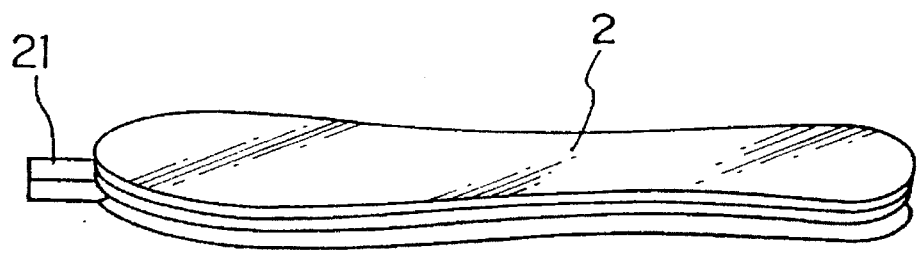

Reference will be made to the steps of making the cast by means of the instruments exemplified herein. The bellows bag 2 is closed at an air hole 21 as seen in FIG. 3 and is disposed within a protecting case 20 comprising a hard resin as illustrated in FIG. 1. A foot 3 is then put on the bellows bag 2, followed by wrapping the casting plaster on the foot in an ordinary sequence and hardening it. When wrapping and hardening the casting plaster, a considerable pressure is burdened on the bellows bag 2, however it may perfectly maintain its shape against the pressuring force, since it is placed within the hard protecting case 20 and the air hole 21 is tightened. When the air hole 21 is opened after the plaster 1 is solidifed, the bellows bag 2 is made to freely expand and contract as is seen in FIG. 4, and the leg cast having the excellent load removing effect is accomplished.

The protecting case 20 serves to protect the soft and elastic bellows bag 2 against the cast 1 wrapped around the patient's leg, and due to this protecting service, the bellows bag 2 may expand and contract vertically (along the length of the shin bone) even by a weak pressure within the cast 1.

Figure 2A:
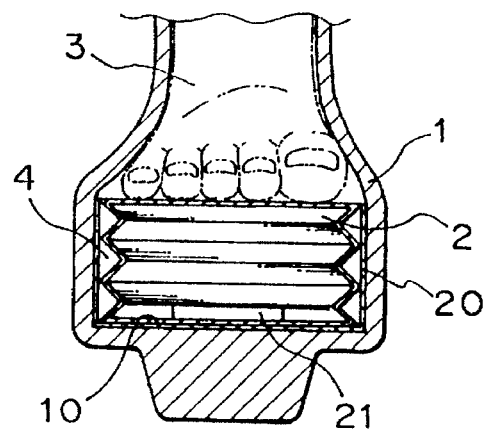
FIG. 2 shows the using condition of the cast provided by the first embodiment, in which (a) is a front view of this condition, (b) is a plane view of the same, and (c) is a side view thereof.
Figure 2B:
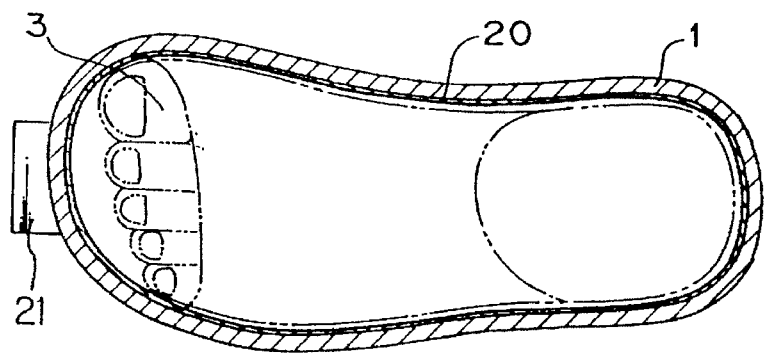
Figure 2C:
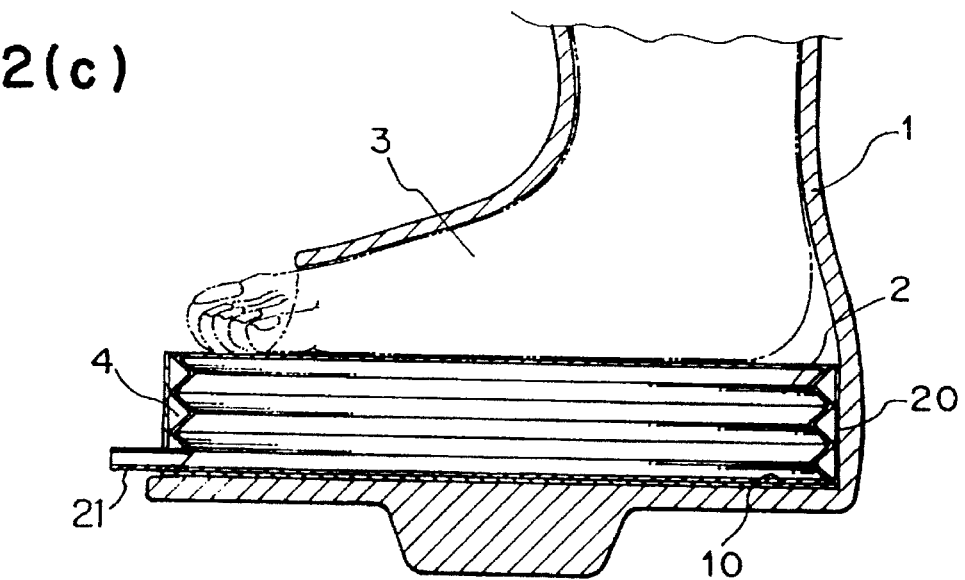

The cast 1 exemplified herein is, as shown in FIG. 2, defined with the space 4 between the sole of the foot 3 and the bottom 10 of the cast 1, and the protecting case 20 made of the hard synthetic resin is disposed in the space 4, within which the bellows bag 2 is placed. The bellows bag 2 communicates with an external through the air hole 21, and expands and contracts in response to movings of the foot as the patient walks as burdened. Therefore, if walking with the present cast 1, the bellows bag 2 placed in the space 4 is pressured and easily shrinked, and the foot 3 moderately moves along the length of the shin bone (in the loading direction) within the space 4, and this moving absorbs the loading force by the walking burden. Thus, as will be later exemplified, the enough load removing effect may be provided.

Figure 5A:
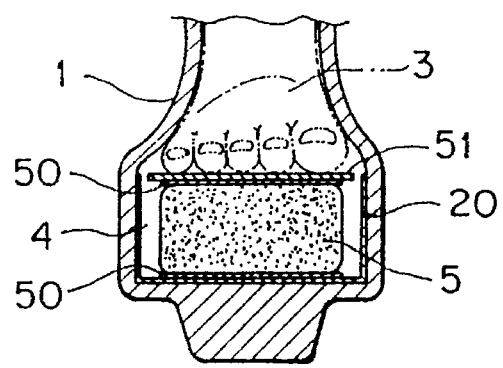
FIG. 5 shows a second embodied instrument, in which (a) is a front view of this embodiment, (b) is a plane view of the same, and (c) is a side view thereof.
Figure 5B:
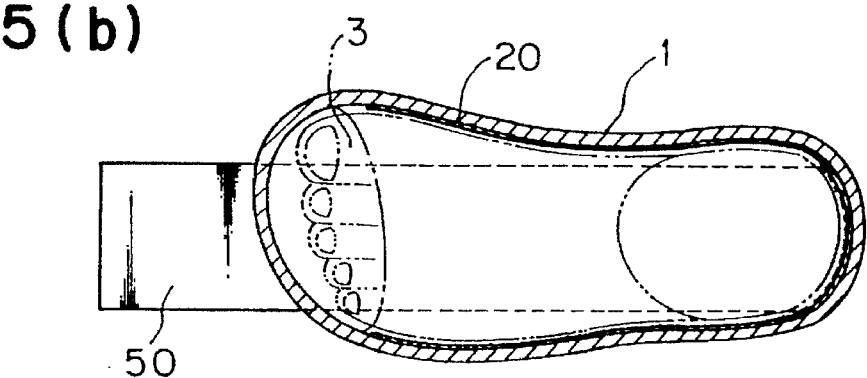
Figure 5C:
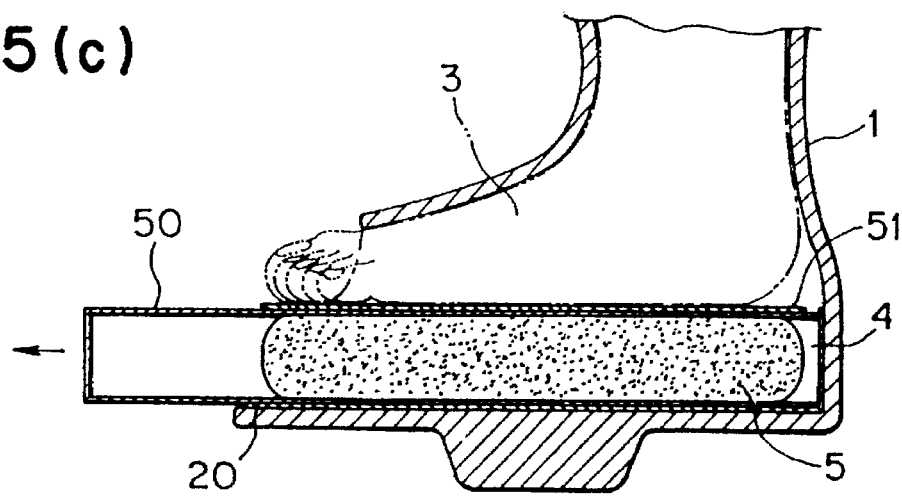
Figure 6A:
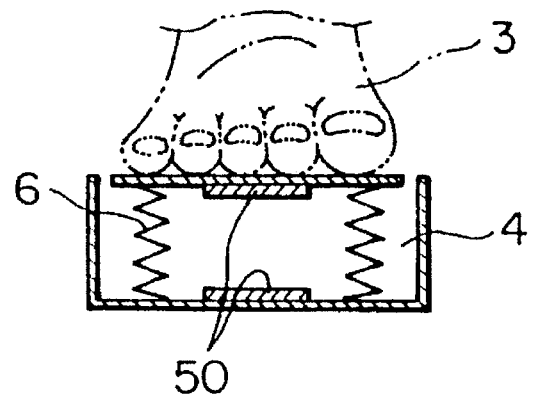
FIG. 6 shows a third embodied instrument, in which (a) is a front view illustrating an expansion of the spring, and (b) is a plane view illustrating a contraction of the same.
Figure 6B:
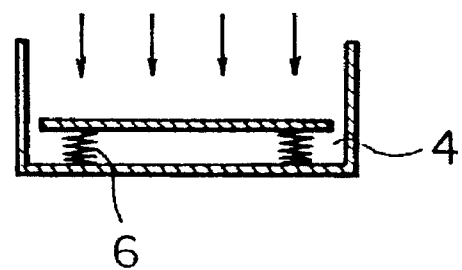

FIG. 5 illustrates the second embodiment, and FIG. 6 shows the third embodiment, and these embodiments employ the sponge and the spring respectively, in place of the bellows bag 2 of the first embodiment.

A further explanation will be made to a preparing process of the cast with the instrument of the second embodiment. A space holding instrument 50 is inserted into a front opening part of the protecting case 20, said space holding instrument being of a rectangle opening one of vertical sides in cross section (⊐) and holding a sponge 5 with its upper and lower sides. A bottom plate 51 is placed on an upper plate of the space holding instrument 50, and the foot 3 is put on the bottom plate 51, followed by wrapping the casting plaster around the patient's foot by an ordinary means.

The space holding instrument 50 is got out after the plaster has been solidified. Then, the space 4 is defined between the sole of the foot 3 and the bottom of the cast 1, and the sponge 5 elastically acts within the space 4. Thus, the cast is completed. The process by the third embodiment is similar to the second embodiment, in which depending upon the space holding instrument 50, the space 4 is formed similarly therebetween, and a spring 5 expands and contracts within the space 4.

Also in the use of the cast 1 produced by these embodiments, when walking, the foot 3 moderately moves within the cast along the length of the shin bone (in the loading direction), so that the loading force caused by the walking burden is fully absorbed.

Figure 7A:
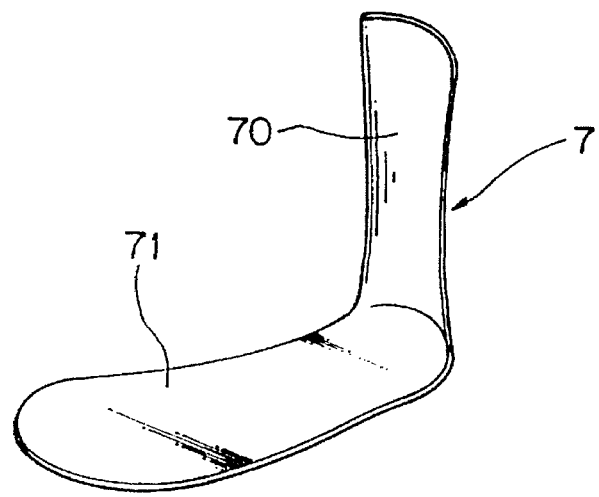
FIG. 7 shows a fourth embodied instrument, in which (a) is a perspective view of this embodiment, (b) is a side view of the same, and (c) is the using condition thereof.
Figure 7B:
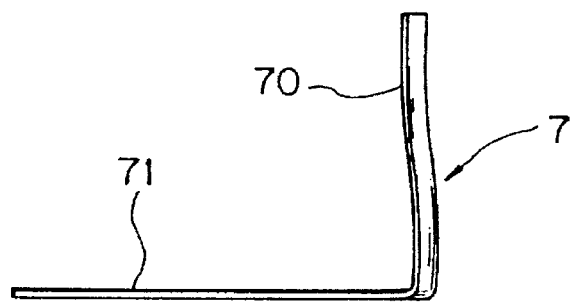
Figure 7C:
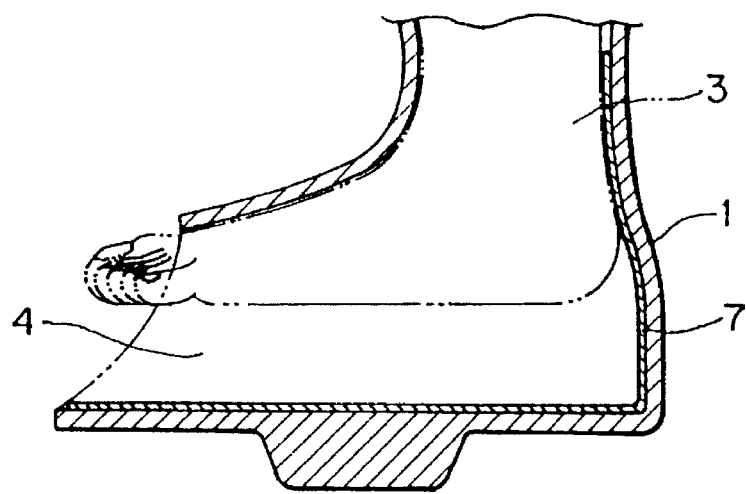

FIG. 7 illustrate a fourth embodiment, and this is different from the above mentioned first to third embodiments, and only forms the space between the sole of the foot 3 and the bottom of the cast 1. A protecting plate 7 of this embodiment is L shaped in cross section of a bent plate member comprising a side 70 contacting a heel of the foot and a bottom 71 contacting the bottom of the cast 1 after having been solidified.

The cast preparing process depending upon this instrument brings the heel to the side 70 such that a space is formed between the sole of the foot 3 and the bottom 71 of the protecting plate, and it is sufficient to wrap and solidify the casting plaster under a condition that the lower portion of the side 70 extends downward than the heel.

The present embodiment does not employ any intermediates such as the bellows, the spring or the sponge between the sole of the foot and the bottom of the cast, however the cast of this embodiment can also make the space for avoiding the push-up, and bring about the satisfied load removing effect by moving of the foot within the space while walking.

Figure 8:
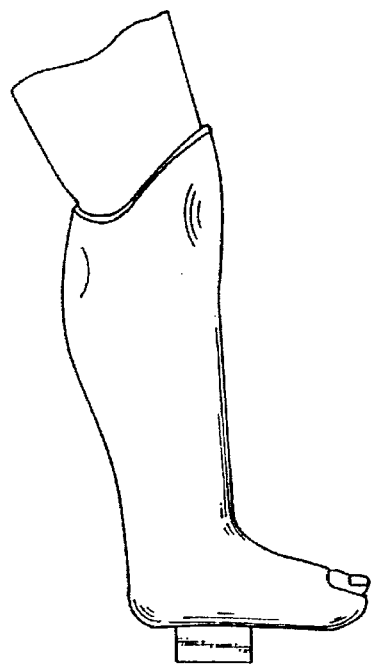
FIG. 8 is an explanatory view showing a conventional leg cast (PTB cast)
Figure 9:
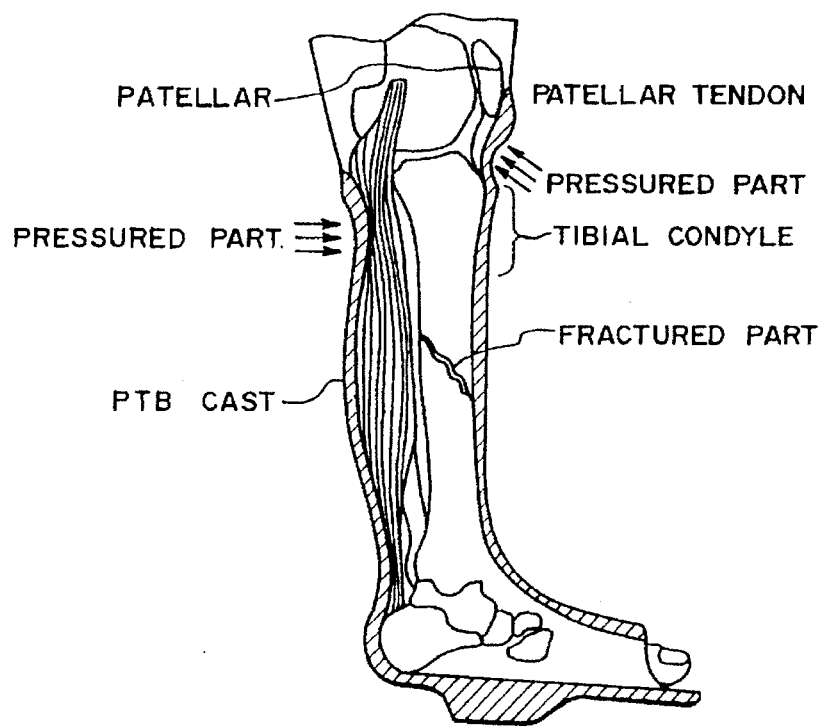
FIG. 9 shows parts aiming at supporting of a patient's human body weight (pressuring parts) in the above conventional leg cast (PTB cast).

With respect to the above embodiments, the load removing effects were tested using the dynamic foot pressure analysis system in comparison with the foregoing cast shown in FIGS. 8 and 9.

The prior PTB cast of FIGS. 8 an 9 showed that the load removing effect was only 30.5% of the human body weight, while the load removing effect of the present invention when the cast having the space of 1 cm thickness was 55.9%, that in a case of 1.5 cm was 65.8%, that of 2.5 cm was 93.7%, and that of 3 cm was 100% which was the perfect load removing effect.

As explained at length, the leg casts provided by means of the inventive instruments bring about remarkable results to largely improve the load removing effect.

In addition, if using, during the healing treatment, the cast which may be provided by means of the instrument made of the elastic member which may vary the space, the following load removing effect may be controlled. That is, for healing the tibial fracture, the sufficient load removing effect is required immediately after suffering from the tibial fracture. It is said that a callus appears around the fractured part as a time goes, and a moderate burden to the fractured part advantageously acts on the bone formation. However, the prior cast did not bring about the sufficient load removing effect required at a beginning period of curing the fractured bone, and besides it was impossible to control the load removing effect in accordance with the curing progress. In contract, in the present invention, as above exemplified, the load removing effect can be varied by changing the thickness of the elastic member. Therefore, if using the elastic members of different thicknesses in response to the curing progress at good timing, the load removing effect may be controlled, and it may be served as an optimum curing instrument.

What is claimed is:

1. A load removing leg cast for surrounding and supporting the lower leg and foot of a patient comprising, a leg surrounding plaster cast portion for surrounding and supporting the lower leg of a patient and a plaster cast bottom portion including an interior bottom base portion, and load removing means for reducing the loading forces upon a patient's lower leg during the imposition of reactive loading forces upon the cast, said load removing means disposed within a space between the interior base portion and the sole of a patient's foot and including an elastic member comprising a bellows bag formed of soft resin lying upon said interior base portion and extending within the space between the interior base portion and the sole of a patient's foot.

2. A load removing leg cast for surrounding and supporting the lower leg and foot of a patient comprising, a leg surrounding plaster cast portion for surrounding and supporting the lower leg of a patient and a plaster cast bottom portion including an interior bottom base portion, a rigid protective casing having a substantially planar casing base and casing sidewalls extending from the casing base, said protective casing lying upon said interior bottom base portion, and load removing means for reducing the loading forces upon a patient's lower leg during the imposition of reactive loading forces upon the cast, said load removing means disposed within a space between said substantially planar casing base and the sole of a patient's foot and including an elastic member disposed within said protective casing and lying upon said casing base, said elastic member comprising a bellows bag formed of soft resin and including an air hole for enabling air to pass into and out of said bellows bag, and wherein said protective casing includes an opening adjacent said bellows bag air hole to enable the air passage.

* * * * *